United States Patent [19]

Tanabe et al.

[11] Patent Number: 5,476,957
[45] Date of Patent: Dec. 19, 1995

[54] SALICYLIC ACID DERIVATIVES

[75] Inventors: Yoshimitsu Tanabe, Yokohama; Yuki Kobayashi, Kamakura; Atsuo Otsuji; Masakatsu Nakatsuka, both of Yokohama; Akihiro Yamaguchi, Kamakura, all of Japan

[73] Assignee: Mitsui Toatsu Chemicals, Inc., Tokyo, Japan

[21] Appl. No.: 338,225

[22] Filed: Nov. 9, 1994

Related U.S. Application Data

[63] Continuation of Ser. No. 301,428, Sep. 9, 1994, abandoned, which is a continuation-in-part of Ser. No. 108,500, Aug. 18, 1993, Pat. No. 5,346,878, which is a continuation-in-part of Ser. No. 946,694, Sep. 18, 1992, Pat. No. 5,306,688.

[30] Foreign Application Priority Data

Sep. 24, 1991 [JP] Japan .................... 3-243201
Jun. 26, 1992 [JP] Japan .................... 4-168744

[51] Int. Cl.⁶ .................... C07F 3/02; C07F 3/04; C07F 3/06; C07F 15/00
[52] U.S. Cl. .................... 556/28; 556/49; 556/50; 556/131; 556/132; 556/134; 556/135; 556/147; 556/148; 556/150; 556/183; 556/184; 558/234; 558/235; 558/241; 560/29
[58] Field of Search .................... 556/28, 49, 50, 556/131, 132, 134, 135, 147, 148, 150, 183, 184; 558/234, 235, 241; 560/29

[56] References Cited

U.S. PATENT DOCUMENTS

| | | | |
|---|---|---|---|
| 4,999,333 | 3/1991 | Usami et al. | 503/209 |
| 5,045,427 | 9/1991 | Hara | 430/138 |
| 5,286,703 | 2/1994 | Wachi et al. | 503/221 |
| 5,306,688 | 4/1994 | Tanabe et al. | 503/210 |
| 5,314,859 | 5/1994 | Takahashi et al. | 503/207 |
| 5,346,878 | 9/1994 | Nakatsuka et al. | 503/209 |

FOREIGN PATENT DOCUMENTS

| | | |
|---|---|---|
| 0253666 | 1/1988 | European Pat. Off. . |
| 0534257 | 3/1993 | European Pat. Off. . |
| 0263037 | 1/1949 | Switzerland . |

OTHER PUBLICATIONS

CRC Handbook of Chemistry and Physics, 63rd Ed., CRC Press pp. C–508 (1982–1983).
Baker et al., Journal of Pharmaceutical Sciences, vol. 52, No. 10, pp. 927–933 (1963).

*Primary Examiner*—Porfirio Nazario-Gonzalez
*Attorney, Agent, or Firm*—Millen, White, Zelano, & Branigan

[57] ABSTRACT

The heat-sensitive recording material disclosed comprises a colorless or pale colored dyestuff precursor, one or more salicylic acid derivative of the formula (1) or metal salt of the derivative and an aliphatic amide compound having 18~60 carbon atoms in molecular structure, and is excellent in thermal response and preservation stability of white portions and images.

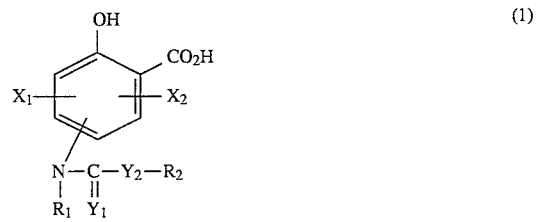

wherein $X_1$ and $X_2$ are a hydrogen atom, a halogen atom, an alkyl group, an alkoxy group, an aralkyl group or an aryl group, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group.

15 Claims, No Drawings

SALICYLIC ACID DERIVATIVES

CROSS-REFERENCE TO RELATED APPLICATION

This is a continuation of application Ser. No. 08/301,428, filed Sep. 9, 1994, now abandoned, filed as a continuation-in-part of application Ser. No. 08/108,500, now U.S. Pat. No. 5,346,878 filed Aug. 18, 1993, as a continuation-in-part of application Ser. No. 07/946,694, filed Sep. 18, 1992, now U.S. Pat. No. 5,306,688, whose disclosures are incorporated herein by reference.

BACKGROUND OF THE INVENTION

1. Field of the Invention

The present invention relates to a novel polyvalent metal salt of a salicylic acid derivative and a process for their production.

2. Related Art of the Invention

Heat-sensitive recording materials generally have a heat-sensitive recording layer on a substrate and the recording layer comprises as principal components a usually colorless or pale colored dyestuff precursor which is the electron donor and a developer which is an electron acceptor. when the recording materials are heated with a thermal head, pot-pen or laser beam, recording images can be obtained by an instantaneous reaction between the dyestuff precursor and the developer.

These recording materials are disclosed, for example, in Japanese Patent Publication SHO 43-4160 and 45-14039, and have advantages that a record can be obtained with relatively simple equipment, maintenance can be conducted with ease, and noise is inhibited. As a result, these heat-sensitive recording materials are used in a broad range of fields such as measuring instrument recorders, facsimiles, printers, computer terminals, labels and automatic ticket vendors.

Heat-sensitive recording materials obtained by using conventional, electron donating colorless dyestuff precursors and electron accepting compounds have characteristics such as high color density. On the other hand, these recording materials have disadvantages that recorded images fade away when they are kept in contact with plastics such as polyvinyl chloride as plasticizers and additives that are usually contained in them migrate to the recording materials, that the preservation characteristic of the recorded images is inferior because the color of these images is deteriorated by contact with chemicals contained in food and cosmetics, or that the color of marks put on them using a marker on white portions change or the marking causes color development. Consequently, these recording materials are restricted in the field of use, and improvement of these recording materials has been strongly desired.

As a means for improving the preservation characteristic of the recorded images and white portions, heat-sensitive recording materials using as the electron accepting compound salicylic acid derivatives having a substituent such as an alkyl group, aralkyl group, alkyloxy group, and aryl group or using metal salts thereof have been proposed in Japanese Laid-Open Patent SHO 62-169681, 63-22683 and 63-95977.

However, the salicylic acid derivatives described in these patents provide unsatisfactory preservation characteristic of developed images, insufficient preservation stability of white portions, and additionally low coloring sensitivity. Thus, these salicylic acid derivatives have been difficult to serve as heat-sensitive recording materials in practical high speed recording.

SUMMARY OF THE INVENTION

The object of the invention is to provide a heat-sensitive recording material having excellent thermal response and preservation stability of white portions and images.

A composition of the invention is a polyvalent metal salt of a salicylic acid derivative represented by the formula (1):

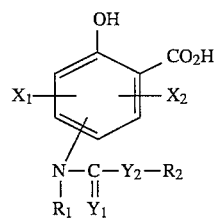

(1)

wherein $X_1$ and $X_2$ are a hydrogen atom, a halogen atom, an alkyl group, an alkoxy group, an aralkyl group, or an aryl group, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, or a divalent, trivalent or tetravalent metal salt of said salicylic acid derivative, further comprising an aliphatic amide compound having 18~60 carbon atoms in molecular structure and being excellent in thermal response and preservation stability of white portions and images.

A process aspect of the invention is a process for preparing a salicylic acid derivative represented by the formula (1) as defined above, comprising reacting a compound represented by the formula (2)

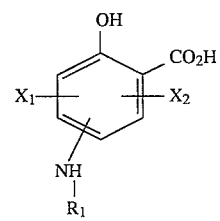

(2)

wherein $X_1$, $X_2$ and $R_1$ have the same values as above, with a compound represented by the formula (3):

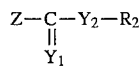

(3)

wherein $Y_1$, $Y_2$ and $R_1$ have the same values as above and Z is a halogen atom, in the presence of an alcohol-based solvent.

The heat-sensitive recording material aspect of the invention is prepared by using the salicylic acid derivative of formula (1) or the metal salt of the derivative in combination with the aliphatic amide compound having 18~60 carbon atoms in the molecular structure, and has further improved thermal response in addition to thermal response and preservation stability of developed images which are essential properties of the salicylic acid derivative of the formula (1) or the metal salt of the derivative as the electron accepting compound for use in the heat-sensitive recording material.

That is, the invention provides a heat-sensitive recording material which is particularly excellent in thermal response, also excellent in preservation stability of white portions and images, and can be compatible with practical high speed recording.

DETAILED DESCRIPTION OF THE INVENTION

The principal electron accepting compound used in the invention is a salicylic acid derivative represented by the formula (1) and/or a metal salt of the salicylic acid derivative.

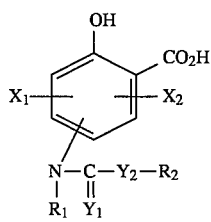

(1)

wherein $X_1$ and $X_2$ are a hydrogen atom, a halogen atom, an alkyl group, an alkoxy group, an aralkyl group or an aryl group, $Y_1$ and $Y_2$ are an oxygen or a sulfur atom, $R_1$ is a hydrogen atom, an alkyl group, an aralkyl group or an aryl group, and $R_2$ is an alkyl group, an alkenyl group, an aralkyl group or an aryl group.

The salicylic acid derivative and the metal salt of the derivative which can be used in the invention have following atoms and groups in the formula (1).

$X_1$ and $X_2$ are a hydrogen, an alkyl, alkoxy, aralkyl or aryl group or halogen atom, preferably hydrogen, $C_1$~$C_{20}$ alkyl, $C_5$~$C_{14}$ alicyclic, $C_1$~$C_{20}$ alkoxy, $C_7$~$C_{20}$ aralkyl, phenyl, fluorine, chlorine or bromine, more preferably hydrogen, $C_1$~$C_4$ alkyl, cyclohexyl, $C_1$~$C_4$ alkoxy, benzyl, α-methylbenzyl, cumyl, phenyl or chlorine, and most preferably hydrogen.

$Y_1$ and $Y_2$ are a oxygen or sulfur atom, and preferably $Y_1$ is oxygen.

$R_1$ is a hydrogen atom, an alkyl, aralkyl or aryl group, preferably hydrogen, $C_1$~$C_{20}$ alkyl, $C_5$~$C_{14}$ alicyclic, $C_7$~$C_{20}$ aralkyl, phenyl or substituted phenyl, more preferably hydrogen, $C_1$~$C_8$ alkyl, cyclopentyl, cyclohexyl, cycloheptyl, benzyl or phenyl, further preferably hydrogen, $C_1$~$C_4$ alkyl or phenyl, and most preferably hydrogen.

$R_2$ is an alkyl, alkenyl, aralkyl or aryl group, preferably alkyl or substituted alkyl, alicyclic or substituted alicyclic, alkenyl or substituted alkenyl, cyclic alkenyl or substituted cyclic alkenyl, aralkyl or substituted aralkyl, phenyl or substituted phenyl, naphthyl or substituted naphthyl, or heteroaromatic or substituted heteroaromatic.

The alkyl or alkenyl represented by $R_2$ can be monosubstituted or polysubstituted.

The substituents include, for example, $C_1$~$C_{20}$ alkoxy, $C_2$~$C_{20}$ alkoxyalkyloxy, $C_2$~$C_{20}$ alkenyloxy, $CC_7$~$C_{20}$ aralkyloxy, $C_8$~$C_{20}$ aralkyloxyalkoxy, $C_6$~$C_{20}$ aryloxy, $C_7$~$C_{20}$ aryloxyalkoxy, $C_8$~$C_{20}$ arylalkenyl, $C_9$~$C_{20}$ aralkylalkenyl, $C_1$18 $C_{20}$ alkylthio, $C_2$~$C_{20}$ alkoxyalkylthio, $C_2$~$C_{20}$ alkylthioalkylthio, $C_2$~$C_{20}$ alkenylthio, $C_7$~$C_{20}$ aralkylthio, $C_8$~$C_{20}$ aralkyloxyalkylthio, $C_8$~$C_{20}$ aralkylthioalkylthio, $C_6$~$C_{20}$ arylthio, $C_7$~$C_{20}$ aryloxyalkylthio, $C_7$~$C_{20}$ arylthioalkylthio, heteroalicyclic, and halogen.

Further, aryl which is included in these substituents can be substituted with $C_1$~$C_6$ alkyl, $C_1$~$C_6$ alkoxy, $C_1$~$C_6$ alkylthio, $C_7$~$C_{10}$ aralkyl, $C_7$~$C_{10}$ aralkyloxy, hydroxyl or halogen.

The aralkyl or aryl represented by $R_2$ can be monosubstituted or polysubstituted.

Exemplary substituents include, $C_1$~$C_{20}$ alkyl, $C_2$~$C_{20}$ alkenyl, $C_7$~$C_{20}$ aralkyl, $C_6$~$C_{20}$ aryl, $C_1$~$C_{20}$ alkoxy, $C_2$~$C_{20}$ alkoxyalkyl, $C_2$~$C_{20}$ alkoxyalkyloxy, $C_2$~$C_{20}$ alkenyloxy, $C_3$~$C_{20}$ alkenyloxyalkyl, $C_3$~$C_{20}$ alkenyloxyalkyloxy, $C_7$~$C_{20}$ aralkyloxy, $C_8$~$C_{20}$ aralkyloxyalkyl, $C_8$~$C_{20}$ aralkyloxyalkyloxy, $C_6$~$C_{20}$ aryloxy, $C_7$~$C_{20}$ aryloxyalkyl, $C_7$~$C_{20}$ aryloxyalkyloxy, $C_2$~$C_{20}$ alkylcarbonyl, $C_3$~$C_{20}$ alkenylcarbonyl, $C_8$~$C_{20}$ aralkylcarbonyl, $C_7$~$C_{20}$ arylcarbonyl, $C_2$~$C_{20}$ alkoxycarbonyl, $C_3$~$C_{20}$ alkenyloxycarbonyl, $C_8$~$C_{20}$ aralkyloxycarbonyl, $C_7$~$C_{20}$ aryloxycarbonyl, $C_2$~$C_{20}$ alkylcarbonyloxy, $C_3$~$C_{20}$ alkenylcarbonyloxy, $C_8$~$C_{20}$ aralkylcarbonyloxy, $C_7$~$C_{20}$ arylcarbonyloxy, $C_{14}$~$C_{20}$ aralkyloxyaralkyl, $C_1$~$C_{20}$ alkylthio, $C_7$~$C_{20}$ aralkylthio, $C_6$~$C_{20}$ arylthio, nitro, formyl, halogen, hydroxy and cyano.

Aryl which is present in these substituents can be further substituted with $C_1$~$C_6$ alkyl, $C_1$~$C_6$ alkoxy, $C_1$~$C_6$ alkylthio, $C_7$~$C_{10}$ aralkyl, $C_7$~$C_{10}$ aralkyloxy, hydroxy or halogen.

Preferred $R_2$ is nonsubstituted or substituted alkyl having from 1 to 24 total carbon atoms, nonsubstituted or substituted alkenyl having from 2 to 24 total carbon atoms, nonsubstituted or substituted aralkyl having from 7 to 24 total carbon atoms, or nonsubstituted or substituted aryl having from 6 to 24 total carbon atoms.

The compound represented by the formula (1) in the invention has a carbamate group on a salicylic acid skeleton. The carbamate group is located on the position 3, 4, 5 or 6, preferably on the position 3, 4 or 5, most preferably on the position 4 or 5 in the salicylic acid skeleton. That is, a more preferred salicylic acid derivative is represented by the formula (1-a):

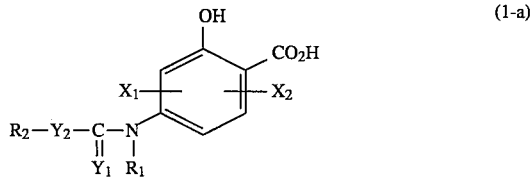

(1-a)

wherein $X_1$, $X_2$, $Y_1$, $Y_2$, $R_1$ and $R_2$ are the same as above, or by the formula (1-b):

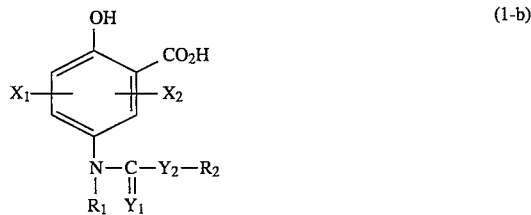

(1-b)

wherein $X_1$, $X_2$, $Y_1$, $Y_2$, $R_1$ and $R_1$ are the same as above.

A most preferred salicylic acid derivative is represented by the formula (1-c):

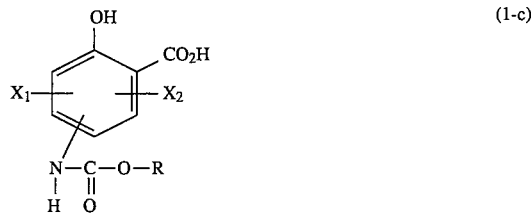

(1-c)

wherein $X_1$ and $X_2$ are the same as above, R is an alkyl group, an alkenyl group, an aralkyl group or an aryl group.

R in the formula (1-c) is an alkyl group such as methyl, ethyl, n-butyl, n-octyl, n-decyl, n-octadecyl, iso-butyl, iso-pentyl or cyclohexyl; an alkenyl group such as alkyl; an aralkyl group such as benzyl or substituted benzyl; or an aryl group such as phenyl or substituted phenyl.

Exemplary salicylic acid derivatives represented by the formula (1) and the metal salts of the derivatives that can be used for the invention will be enumerated below. However, it is to be understood that the invention is not limited by the following compounds.

Compound 1) 3-(isopropyloxycarbonylamino)salicylic acid
2) 3-(isopentyloxycarbonylamino)salicylic acid
3) 3-(n-hexyloxycarbonylamino)salicylic acid
4) 3-(n-octyloxycarbonylamino)salicylic acid
5) 3-(n-decyloxycarbonylamino)salicylic acid
6) 3-[(4'-methylcyclohexyl)oxycarbonylamino]salicylic acid
7) 3-[(2'-cyclohexylethyl)oxycarbonylamino]salicylic acid
8) 3-(allyloxycarbonylamino)salicylic acid
9) 3-[(2'-hexenyl)oxycarbonylamino]salicylic acid
10) 3-[(2'-ethoxyethyl)oxycarbonylamino]salicylic acid
11) 3-[(3'-n-hexyloxypropyl)oxycarbonylamino]salicylic acid
12) 3-[(2'-benzyloxyethyl)oxycarbonylamino]salicylic acid
13) 3-(phenoxymethyloxycarbonylamino)salicylic acid
14) 3-[(2'-phenoxyethyl)oxycarbonylamino]salicylic acid
15) 3-[(2'-(4-chlorophenyl)oxyethyloxycarbonylamino]salicylic acid
16) 3-[2'-(4-methoxyphenyl)oxyethyloxycarbonylamino]salicylic acid
17) 3-[(2'-phenoxyethoxyethyl)oxycarbonylamino]salicylic acid
18) 3-(cinnamyloxycarbonylamino)salicylic acid
19) 3-[(2'-n-butylthioethyl)oxycarbonylamino]salicylic acid
20) 3-[(2'-methoxyethylthioethyl)oxycarbonylamino]salicylic acid
21) 3-[(2'-allylthioethyl)oxycarbonylamino]salicylic acid
22) 3-[(2'-benzylthioethyl)oxycarbonylamino]salicylic acid
23) 3-[(2'-phenylthioethyl)oxycarbonylamino]salicylic acid
24) 3-[(7'-chloroheptyl)oxycarbonylamino]salicylic acid
25) 3-(benzyloxycarbonylamino)salicylic acid
26) 3-[(4'-methylbenzyl)oxycarbonylamino]salicylic acid
27) 3-[(4'-chlorobenzyl)oxycarbonylamino]salicylic acid
28) 3-[(3'-phenoxybenzyl)oxycarbonylamino]salicylic acid
29) 3-(phenyloxycarbonylamino)salicylic acid
30) 3-[(2'-naphthyl)oxycarbonylamino]salicylic acid
31) 3-[(3'-furyl)oxycarbonylamino]salicylic acid
32) 3-[(3'-phenylphenyl)oxycarbonylamino]salicylic acid
33) 3-[(4'-methylphenyl)oxycarbonylamino]salicylic acid
34) 3-[(4'-n-butylphenyl)oxycarbonylamino]salicylic acid
35) 3-[(4'-tert-butylphenyl)oxycarbonylamino]salicylic acid
36) 3-[(4'-cyclohexylphenyl)oxycarbonylamino]salicylic acid
37) 3-[(3'-methoxyphenyl)oxycarbonylamino]salicylic acid
38) 3-[(4'-n-butoxyphenyl)oxycarbonylamino]salicylic acid
39) 3-[(4'-n-octyloxyphenyl)oxycarbonylamino]salicylic acid
40) 3-[(4'-phenoxyphenyl)oxycarbonylamino]salicylic acid
41) 3-[(2'-acetylphenyl)oxycarbonylamino]salicylic acid
42) 3-[(4'-allylcarbonylphenyl)oxycarbonylamino]salicylic acid
43) 3-[(4'-phenylcarbonylphenyl)oxycarbonylamino]salicylic acid
44) 3-[(4'-n-butoxycarbonylphenyl)oxycarbonylamino]salicylic acid
45) 3-[(4'-benzyloxyphenyl)oxycarbonylamino]salicylic acid
46) 3-[(4'-acetyloxyphenyl)oxycarbonylamino]salicylic acid
47) 3-[(4'-ethylthiophenyl)oxycarbonylamino]salicylic acid
48) 3-[(4'-fluorophenyl)oxycarbonylamino]salicylic acid
49) 3-[(4'-chlorophenyl)oxycarbonylamino]salicylic acid
50) 3-[(4'-nitrophenyl)oxycarbonylamino]salicylic acid
51) 3-[(4'-formylphenyl)oxycarbonylamino]salicylic acid
52) 3-[(4'-hydroxyphenyl)oxycarbonylamino]salicylic acid
53) 3-[(4'-cyanophenyl)oxycarbonylamino]salicylic acid
54) 3-[(2',4'-dimethylphenyl)oxycarbonylamino]salicylic acid
55) 3-[(3',5'-dichlorophenyl)oxycarbonylamino]salicylic acid
56) 5-methyl-3-(n-hexyloxycarbonylamino)salicylic acid
57) 5-cyclohexyl-3-(phenyloxycarbonylamino)salicylic acid
58) 5-cumyl-3-(n-hexyloxycarbonylamino)salicylic acid
59) 3-(n-octylthiolcarbonylamino)salicylic acid
60) 3-[(4'-chlorobenzyl)thiolcarbonylamino]salicylic acid
61) 3-[(3'-methylphenyl)thiolcarbonylamino]salicylic acid
62) 3-(n-butylthiolthiocarbonylamino)salicylic acid
63) 3-(phenylthiolthiocarbonylamino)salicylic acid
64) 3-[(4'-ethoxyphenyl)thiolthiocarbonylamino]salicylic acid
65) 3-(N-phenyl-N-phenyloxycarbonylamino)salicylic acid
66) 4-(methyloxycarbonylamino)salicylic acid
67) 4-(ethyloxycarbonylamino)salicylic acid
68) 4-(n-propyloxycarbonylamino)salicylic acid
69) 4-(isopropyloxycarbonylamino)salicylic acid
70) 4-(n-butyloxycarbonylamino)salicylic acid
71) 4-(isobutyloxycarbonylamino)salicylic acid
72) 4-(sec-butyloxycarbonylamino)salicylic acid
73) 4-(n-pentyloxycarbonylamino)salicylic acid
74) 4-(isopentyloxycarbonylamino)salicylic acid
75) 4-(n-hexyloxycarbonylamino)salicylic acid
76) 4-(n-heptyloxycarbonylamino)salicylic acid
77) 4-(n-octyloxycarbonylamino)salicylic acid
78) 4-[(2'-ethylhexyl)oxycarbonylamino]salicylic acid
79) 4-(n-nonyloxycarbonylamino)salicylic acid
80) 4-(n-decyloxycarbonylamino)salicylic acid
81) 4-(n-undecyloxycarbonylamino)salicylic acid
82) 4-(n-dodecyloxycarbonylamino)salicylic acid
83) 4-(n-tridecyloxycarbonylamino)salicylic acid
84) 4-(n-tetradecyloxycarbonylamino)salicylic acid
85) 4-(n-pentadecyloxycarbonylamino)salicylic acid
86) 4-(n-hexadecyloxycarbonylamino)salicylic acid
87) 4-(n-heptadecyloxycarbonylamino)salicylic acid
88) 4-(n-octadecyloxycarbonylamino)salicylic acid
89) 4-(cyclopentyloxycarbonylamino)salicylic acid
90) 4-(cyclohexyloxycarbonylamino)salicylic acid
91) 4-[(4'-tert-butylcyclohexyl)oxycarbonylamino]salicylic acid
92) 4-(cycloheptyloxycarbonylamino)salicylic acid
93) 4-(cyclooctyloxycarbonylamino)salicylic acid
94) 4-(cyclohexylmethyloxycarbonylamino)salicylic acid
95) 4-[(2'-tetrahydrofurfuryl)oxycarbonylamino]salicylic acid
96) 4-[(2'-methoxyethyl)oxycarbonylamino]salicylic acid
97) 4-[(2'-n-hexyloxyethyl)oxycarbonylamino]salicylic acid
98) 4-[(2'-n-octyloxyethyl)oxycarbonylamino]salicylic acid
99) 4-[(3'-ethoxypropyl)oxycarbonylamino]salicylic acid
100) 4-[(3'-n-butoxypropyl)oxycarbonylamino]salicylic acid
101) 4-[(3'-n-octyloxypropyl)oxycarbonylamino]salicylic acid
102) 4-[(2'-n-butoxyethoxyethyl)oxycarbonylamino]salicylic acid
103) 4-[(2'-benzyloxyethyl)oxycarbonylamino]salicylic acid
104) 4-[(phenoxymethyl)oxycarbonylamino]salicylic acid 105) 4-[(2'-phenoxyethyl)oxycarbonylamino]salicylic acid
106) 4-[2'-(4-chlorophenyl)oxyethyloxycarbonylamino]salicylic acid
107) 4-[2'-(4-methoxyphenyl)oxyethyloxycarbonylamino]salicylic acid
108) 4-[(2'-phenoxyethoxyethyl)oxycarbonylamino]salicylic acid
109) 4-[(3-n-butylthiopropyl)oxycarbonylamino]salicylic acid
110) 4-[(6-ethylthiohexyl)oxycarbonylamino]salicylic acid
111) 4-[(2-benzylthioethyl)oxycarbonylamino]salicylic acid
112) 4-[(2-phenylthioethyl)oxycarbonylamino]salicylic acid
113) 4-[(2-chloroethyl)oxycarbonylamino]salicylic acid
114) 4-[(9-decenyl)oxycarbonylamino]salicylic acid
115) 4-(benzyloxycarbonylamino)salicylic acid
116) 4-[(4'-methylbenzyl)oxycarbonylamino]salicylic acid
117) 4-[(4'-chlorobenzyl)oxycarbonylamino]salicylic acid
118) 4-[(2'-phenylethyl)oxycarbonylamino]salicylic acid
119) 4-(phenyloxycarbonylamino)salicylic acid
120) 4-[(1'-naphthyl)oxycarbonylamino]salicylic acid
121) 4-[(2'-naphthyl)oxycarbonylamino]salicylic acid
122) 4-[(2'-furyl)oxycarbonylamino]salicylic acid
123) 4-[(4'-phenylphenyl)oxycarbonylamino]salicylic acid
124) 4-[(4'-methylphenyl)oxycarbonylamino]salicylic acid
125) 4-[(3'-methylphenyl)oxycarbonylamino]salicylic acid
126) 4-[(2'-methylphenyl)oxycarbonylamino]salicylic acid
127) 4-[(4'-ethylphenyl)oxycarbonylamino]salicylic acid
128) 4-[(4'-tert-butylphenyl)oxycarbonylamino]salicylic acid
129) 4-[(4'-cyclohexylphenyl)oxycarbonylamino]salicylic acid
130) 4-[(2'-cyclohexylphenyl)oxycarbonylamino]salicylic acid
131) 4-[(4'-cumylphenyl)oxycarbonylamino]salicylic acid
132) 4-[(4'-methoxyphenyl)oxycarbonylamino]salicylic acid
133) 4-[(3'-methoxyphenyl)oxycarbonylamino]salicylic acid
134) 4-[(2'-ethoxyphenyl)oxycarbonylamino]salicylic acid
135) 4-[(4'-n-butoxyphenyl)oxycarbonylamino]salicylic acid
136) 4-[(4'-n-hexyloxyphenyl)oxycarbonylamino]salicylic acid
137) 4-[(4'-benzyloxyphenyl)oxycarbonylamino]salicylic acid
138) 4-[4'-(4-benzyloxycumyl)phenyloxycarbonylamino]salicylic acid
139) 4-[(4'-phenoxyphenyl)oxycarbonylamino]salicylic acid
140) 4-[2'-(6-benzyloxy)naphthyloxycarbonylamino]salicylic acid
141) 4-[(4'-phenylcarbonylphenyl)oxycarbonylamino]salicylic acid
142) 4-[(4'-acetylphenyl)oxycarbonylamino]salicylic acid
143) 4-[(4'-ethoxyphenyl)oxycarbonylamino]salicylic acid
144) 4-[(4'-cyclohexyloxycarbonylphenyl)oxycarbonylamino]salicylic acid
145) 4-[(4'-n-propylcarbonyloxyphenyl)oxycarbonylamino]salicylic acid
146) 4-[(4'-n-methylthiophenyl)oxycarbonylamino]salicylic acid,
147) 4-[(4'-benzylthiophenyl)oxycarbonylamino]salicylic acid
148) 4-[(4'-fluorophenyl)oxycarbonylamino]salicylic acid
149) 4-[(2'-fluorophenyl)oxycarbonylamino]salicylic acid
150) 4-[(4'-chlorophenyl)oxycarbonylamino]salicylic acid
151) 4-[(3'-chlorophenyl)oxycarbonylamino]salicylic acid
152) 4-[(4'-bromophenyl)oxycarbonylamino]salicylic acid
153) 4-[(4'-nitrophenyl)oxycarbonylamino]salicylic acid
154) 4-[(4'-formylphenyl)oxycarbonylamino]salicylic acid
155) 4-[(4'-cyanophenyl)oxycarbonylamino]salicylic acid
156) 4-[(2',4'-dimethylphenyl)oxycarbonylamino]salicylic acid
157) 4-[(3',5'-dimethylphenyl)oxycarbonylamino]salicylic acid
158) 4-[(2',4'-dichlorophenyl)oxycarbonylamino]salicylic acid
159) 4-[(3',5'-dimethoxyphenyl)oxycarbonylamino]salicylic acid
160) 4-[(3'-nitro-4'-chlorophenyl)oxycarbonylamino]salicylic acid
161) 4-[(4'-chloro-2'-methylphenyl)oxycarbonylamino]salicylic acid
162) 4-(n-octylthiolcarbonylamino)salicylic acid
163) 4-(phenylthiolcarbonylamino)salicylic acid
164) 4-[(4'-ethoxyphenylthiol)carbonylamino]salicylic acid
165) 4-(n-hexylthiolthiocarbonylamino)salicylic acid
166) 4-[(4'-methylphenylthiol)thiocarbonylamino]salicylic acid
167) 4-(n-decyloxythiocarbonylamino)salicylic acid
168) 4-(N-n-butyl-N-heptyloxycarbonylamino)salicylic acid
169) 3-ethyl-4-(phenyloxycarbonylamino)salicylic acid
170) 3-chloro-4-(n-butyloxycarbonylamino)salicylic acid
171) 5-(methyloxycarbonylamino)salicylic acid
172) 5-(ethyloxycarbonylamino)salicylic acid
173) 5-(n-propyloxycarbonylamino)salicylic acid
174) 5-(n-butyloxycarbonylamino)salicylic acid
175) 5-(isobutyloxycarbonylamino)salicylic acid
176) 5-(n-pentyloxycarbonylamino)salicylic acid
177) 5-(isopentyloxycarbonylamino)salicylic acid
178) 5-(n-hexyloxycarbonylamino)salicylic acid
179) 5-(n-heptyloxycarbonylamino)salicylic acid
180) 5-(n-octyloxycarbonylamino)salicylic acid
181) 5-[(2'-ethylhexyl)oxycarbonylamino]salicylic acid
182) 5-(n-nonyloxycarbonylamino)salicylic acid
183) 5-(n-decyloxycarbonylamino)salicylic acid
184) 5-(n-undecyloxycarbonylamino)salicylic acid
185) 5-(n-dodecyloxycarbonylamino)salicylic acid
186) 5-(n-tetradecyloxycarbonylamino)salicylic acid
187) 5-(n-hexadecyloxycarbonylamino)salicylic acid
188) 5-(cyclohexyloxycarbonylamino)salicylic acid
189) 5-[(4'-methylcyclohexyl)oxycarbonylamino]salicylic acid
190) 5-[(4'-tert-butylcyclohexyl)oxycarbonylamino]salicylic acid
191) 5-[(2'-cyclohexylethyl)oxycarbonylamino]salicylic acid
192) 5-(cyclooctyloxycarbonylamino)salicylic acid
193) 5-[(2'-tetrahydrofurfuryl)oxycarbonylamino]salicylic acid
194) 5-[(2'-methoxyethyl)oxycarbonylamino]salicylic acid
195) 5-[(2'-n-hexyloxyethyl)oxycarbonylamino]salicylic acid
196) 5-[(3'-ethoxypropyl)oxycarbonylamino]salicylic acid
197) 5-[(3'-isopropoxypropyl)oxycarbonylamino]salicylic acid
198) 5-[(2'-methoxyethoxyethyl)oxycarbonylamino]salicylic acid
199) 5-(phenoxymethyloxycarbonylamino)salicylic acid
200) 5-(2'-phenoxyethyloxycarbonylamino)salicylic acid
201) 5-[2'-(4-chlorophenyl)oxyethyloxycarbonylamino]salicylic acid 202) 5-[2'-(4-methoxyphenyl)oxyethyloxycarbonylamino]salicylic acid
203) 5-[(2'-phenoxyethoxyethyl)oxycarbonylamino]salicylic acid
204) 5-[(2'-n-hexylthioethyl)oxycarbonylamino]salicylic acid
205) 5-[(2'-phenylthioethyl)oxycarbonylamino]salicylic acid
206) 5-(2'-chloroethyloxycarbonylamino)salicylic acid
207) 5-(5'-hexenyloxycarbonylamino)salicylic acid
208) 5-(benzyloxycarbonylamino)salicylic acid
209) 5-[(4'-methylbenzyl)oxycarbonylamino]salicylic acid
210) 5-[(4'-chlorobenzyl)oxycarbonylamino]salicylic acid
211) 5-[(2'-phenylethyl)oxycarbonylamino]salicylic acid
212) 5-(phenyloxycarbonylamino)salicylic acid
213) 5-[(2'-naphthyl)oxycarbonylamino]salicylic acid
214) 5-[(4'-phenylphenyl)oxycarbonylamino]salicylic acid
215) 5-[(3'-methylphenyl)oxycarbonylamino]salicylic acid
216) 5-[(4'-ethylphenyl)oxycarbonylamino]salicylic acid
217) 5-[(4'-cyclohexylphenyl)oxycarbonylamino]salicylic acid
218) 5-[(4'-cumylphenyl)oxycarbonylamino]salicylic acid
219) 5-[(4'-methoxyphenyl)oxycarbonylamino]salicylic acid
220) 5-[(3'-ethoxyphenyl)oxycarbonylamino]salicylic acid
221) 5-[(4'-n-butoxyphenyl)oxycarbonylamino]salicylic acid
222) 5-[(4'-phenoxyphenyl)oxycarbonylamino]salicylic acid
223) 5-[(4'-acetylphenyl)oxycarbonylamino]salicylic acid
224) 5-[(4'-methoxycarbonylphenyl)oxycarbonylamino]salicylic acid
225) 5-[(4'-ethylcarbonyloxyphenyl)oxycarbonylamino]salicylic acid
226) 5-[(4'-ethylthiophenyl)oxycarbonylamino]salicylic acid
227) 5-[(4'-phenylthiophenyl)oxycarbonylamino]salicylic acid
228) 5-[(4'-fluorophenyl)oxycarbonylamino]salicylic acid
229) 5-[(3'-fluorophenyl)oxycarbonylamino]salicylic acid
230) 5-[(4'-chlorophenyl)oxycarbonylamino]salicylic acid
231) 5-[(3'-chlorophenyl)oxycarbonylamino]salicylic acid
232) 5-[(2'-chlorophenyl)oxycarbonylamino]salicylic acid
233) 5-[(2'-formylphenyl)oxycarbonylamino]salicylic acid
234) 5-[(2'-cyanophenyl)oxycarbonylamino]salicylic acid
235) 5-[(2',4'-dimethylphenyl)oxycarbonylamino]salicylic acid
236) 5-[(3',5'-dimethylphenyl)oxycarbonylamino]salicylic acid
237) 5-[(3'-nitro-4'-chlorophenyl)oxycarbonylamino]salicylic acid
238) 5-(n-butylthiolcarbonylamino)salicylic acid
239) 5-(phenylthiolcarbonylamino)salicylic acid
240) 5-[(2'-naphthylthiol)carbonylamino]salicylic acid
241) 5-[(4'-methylphenylthiol)carbonylamino]salicylic acid
242) 5-(n-heptylthiolthiocarbonylamino)salicylic acid
243) 5-(n-dodecylthiolthiocarbonylamino)salicylic acid
244) 5-(n-pentyloxythiocarbonylamino)salicylic acid
245) 5-[(4'-chlorophenyl)oxythiocarbonylamino]salicylic acid
246) 5-(N-methyl-N-phenyloxycarbonylamino)salicylic acid
247) 3-methyl-5-(methyloxycarbonylamino)salicylic acid
248) 3-ethoxy-5-(n-butyloxycarbonylamino)salicylic acid
249) 3-α-methylbenzyl-5-(ethyloxycarbonylamino)salicylic acid
250) 3-phenyl-5-(n-hexyloxycarbonylamino)salicylic acid
251) 6-(n-propyloxycarbonylamino)salicylic acid
252) 6-(isopentyloxycarbonylamino)salicylic acid
253) 6-(n-heptyloxycarbonylamino)salicylic acid
254) 6-[(1'-methylheptyl)oxycarbonylamino]salicylic acid
255) 6-(n-dodecyloxycarbonylamino)salicylic acid
256) 6-[(2',5'-dimethylcyclohexyl)oxycarbonylamino]salicylic acid
257) 6-[(2'-cyclohexylmethyl)oxycarbonylamino]salicylic acid
258) 6-[(3'-butenyl)oxycarbonylamino]salicylic acid
259) 6-[(10'-undecenyl)oxycarbonylamino]salicylic acid
260) 6-[(2'-isopropoxyethyl)oxycarbonylamino]salicylic acid
261) 6-[(3'-cyclohexyloxypropyl)oxycarbonylamino]salicylic acid
262) 6-[(2'-phenethyloxyethyl)oxycarbonylamino]salicylic acid
263) 6-[(2'-phenoxyethyl)oxycarbonylamino]salicylic acid
264) 6-[(2'-(4-chlorophenoxy)ethyloxycarbonylamino]salicylic acid
265) 6-[(3'-n-buthylthiopropyl)oxycarbonylamino]salicylic acid
266) 6-[(3'-(4-methylbenzylthio)propyloxycarbonylamino]salicylic acid
267) 6-[(2'-phenylthioethyl)oxycarbonylamino]salicylic acid
268) 6-[(2'-tetrahydrofurfuryl)oxycarbonylamino]salicylic acid
269) 6-[(2'-chloroethyl)oxycarbonylamino]salicylic acid
270) 6-(benzyloxycarbonylamino)salicylic acid
271) 6-[(4'-chlorobenzyl)oxycarbonylamino]salicylic acid
272) 6-(phenyloxycarbonylamino)salicylic acid
273) 6-[(1'-naphthyl)oxycarbonylamino]salicylic acid
274) 6-[(4'-phenylphenyl)oxycarbonylamino]salicylic acid
275) 6-[(2'-ethylphenyl)oxycarbonylamino]salicylic acid
276) 6-[(4'-tert-butylphenyl)oxycarbonylamino]salicylic acid
277) 6-[(3'-methoxyphenyl)oxycarbonylamino]salicylic acid
278) 6-[(4'-n-hexyloxyphenyl)oxycarbonylamino]salicylic acid
279) 6-[(3'-phenoxyphenyl)oxycarbonylamino]salicylic acid
280) 6-[(4'-ethylcarbonylphenyl)oxycarbonylamino]salicylic acid
281) 6-[(4'-benzylcarbonylphenyl)oxycarbonylamino]salicylic acid
282) 6-[(4'-methoxycarbonylphenyl)oxycarbonylamino]salicylic acid
283) 6-[(4'-methylthiophenyl)oxycarbonylamino]salicylic acid
284) 6-[(3'-fluorophenyl)oxycarbonylamino]salicylic acid
285) 6-[(2'-chlorophenyl)oxycarbonylamino]salicylic acid
286) 6-[(3'-nitrophenyl)oxycarbonylamino]salicylic acid
287) 6-[(2'-formylphenyl)oxycarbonylamino]salicylic acid
288) 6-[(3'-hydroxyphenyl)oxycarbonylamino]salicylic acid
289) 6-[(4'-cyanophenyl)oxycarbonylamino]salicylic acid
290) 6-[(3',4'-dimethylphenyl)oxycarbonylamino]salicylic acid
291) 6-[(2',4'-dichlorophenyl)oxycarbonylamino]salicylic acid
292) 3-ethyl-6-(n-hexyloxycarbonylamino)salicylic acid
293) 3-tert-butyl-6-(phenyloxycarbonylamino)salicylic acid
294) 6-(N-ethyl-N-phenyloxycarbonylamino)salicylic acid
295) 6-(n-octylthiolcarbonylamino)salicylic acid
296) 6-[(4'-methylbenzyl)thiolcarbonylamino]salicylic acid
297) 7)6-[(4'-methylphenyl)thiolcarbonylamino]salicylic acid 298) 8)6-(n-octylthiolthiocarbonylamino)salicylic acid
299) 6-(phenylthiolthiocarbonylamino)salicylic acid
300) 6-[(4'-methoxyphenyl)thiolthiocarbonylamino]salicylic acid The metal salts of the salicylic acid derivatives represented by the formula (1) which is used for the electron accepting compound in the heat-sensitive recording material of the invention include salts of monovalent metals such as sodium, potassium and lithium and polyvalent metals having 2, 3 and 4 valence. In the case of using the metal salt singly as an electron accepting compound, the salt is preferably a metal salt which is difficultly soluble or insoluble in water and composed of a polyvalent metal of 2, 3 and 4 valence, more preferably a salt of the polyvalent metal having 2 or 3 valence.

This process of this invention is characterized by reacting a compound of formula (2) with a compound of formula (3) in the presence of an alcohol-based solvent, i.e., an alcohol-containing solvent, preferably an alcohol having from i to 8 carbon atoms, e.g., methanol, ethanol, propanol, butanol, pentanol, heptanol, octanol, cyclohexanol, methyl cellosolve and ethyl cellosolve. These solvents can be used singly or as a mixture and can be used in combination with other organic solvents. However, when the amount of the alcohol-based solvent is less than 10% by weight, the reaction requires a long time or unreacted compound of formula (2) remains after the reaction. Accordingly, the amount of the alcohol-based solvent is preferably 10% by weight or more, more preferably 30% by weight or more, and most preferably 50% by weight or more of the total amount of the solvent.

Exemplary metal salts are salts of sodium, potassium, lithium, zinc, cadmium, mercury, magnesium, calcium, barium, nickel, tin, gallium, chromium, copper, molybdenum, wolfram, zirconium, strontium, manganese, cobalt, titanium, aluminum and iron, preferably salts of zinc, calcium, barium, nickel, manganese, cobalt and aluminum, more preferably salts of zinc, magnesium, nickel and manganese, most preferably a zinc salt.

The metal salt of the salicylic acid derivative can be used for the heat-sensitive recording material of the invention. The salicylic acid derivative represented by the formula (1) and the metal salt of the derivative can be used singly or as a mixture for the electron accepting compound in the heat-sensitive recording material of the invention. For example, a combination of one or more salicylic acid derivatives and a metal salt of salicylic acid derivative can also be used.

The salicylic acid derivative represented by the formula (1) or the metal salt of the derivative which is used in the invention can be prepared by known processes described, for example, in J.Pharm. Sci., 52,927(1963) and Bull.de.Socie. Chim. France, 1189(1955). That is, the derivative and its metal salt can be suitably prepared, for example, by reacting an aminosalicylic acid derivative with an almost equivalent amount of a chloroformate compound.

The heat-sensitive recording material of the invention is characterized in that the preferred preservation characteristic of developed images, good preservation stability of white portions and very excellent thermal response can be obtained by using the aliphatic amide compound described below in combination with the above salicylic acid derivative or the metal salt of the derivative.

The aliphatic amide compound that can be used in the invention and has 18~60 carbon atoms in the molecular structure is represented by the formula (3):

$$R_3CONH_2 \qquad (3)$$

wherein $R_3$ is an alkyl group or an alkenyl group and has 17~59 carbon, the formula (4):

$$R_4CONHR_5 \qquad (4)$$

wherein $R_4$ is an alkyl group or an alkenyl group, $R_5$ is an alkyl group, an alkenyl group or a hydroxymethyl group, and the sum of carbon atoms in $R_4$ and $R_5$ is 17~59, the formula (5):

$$R_6CONHR_7NHOCR_6 \qquad (5)$$

wherein $R_6$ is an alkyl group or an alkenyl group, $R_7$ is a divalent aliphatic radical and the sum of carbon atoms in $R_6$ and $R_7$ is 16~58, or the formula (6):

$$R_8NHOCR_9CONHR_8 \qquad (6)$$

wherein $R_8$ is an alkyl group or an alkenyl group, $R_9$ is a divalent aliphatic group, and the sum of carbon atoms in $R_8$ and $R_9$ is 16~58.

Exemplary compounds represented by the formula (3) include stearic acid amide, oleic acid amide, behenic acid amide, erucic acid amide, tricosanoic acid amide, lignoceric acid amide, pentacosanoic acid amide, cerotic acid amide and melissic acid amide.

Exemplary compounds represented by the formula (4) include: N-octylpalmitic acid amide, N-methylstearic acid amide, N-ethylstearic acid amide, N-butylstearic acid amide, N-cyclohexylstearic acid amide, N-decylstearic acid amide, N-stearylstearic acid amide, N-oleylstearic acid amide, N-hydroxymethylstearic acid amide and N-hydroxymethylbehenic acid amide.

Exemplary compounds represented by the formula (5) include: ethylenebisstearic acid amide, butylenebisstearic acid amide, pentamethylenebisstearic acid amide, hexamethylenebisoleic acid amide, hexamethylenebisstearic acid amide, hexamethylenebislauric acid amide, hexamethylenebispalmitic acid amide, and octamethylenebispalmitic acid amide.

Exemplary compounds represented by the formula (6) include
N,N'-dihexylsebacic acid amide,
N,N'-dioctyladipic acid amide,
N,N'-dilauryladipic acid amide,
N,N'-dipalmityladipic acid amide,
N,N'-distearylpimelic acid amide,
N,N'-distearylsuberic acid amide,
N,N'-distearylazelaic acid amide,
N,N'-dioleyladipic acid amide,
N,N'-dioleylsebacic acid amide,
N,N'-distearyladipic acid amide, and
N,N'-distearylsebacic acid amide.

These aliphatic amide compounds can be used singly or as a mixture.

When the aliphatic amide compound having 18~60 carbon atoms in the molecular structure is used in combination with an electron accepting compound, that is, the salicylic acid derivative represented by the formula (1) or the metal salt of the derivative, thermal response of the heat-sensitive recording material can be improved without giving an adverse effect on the preservation stability of white portions and images.

When an aliphatic amide compound having 19 or more carbon atoms is used, wet heat resistance (i.e. resistance to heat under a moist environment), which is an attribute of the image preservation stability, is improved as compared with when an aliphatic amide having 18 carbon atoms is used. That is, the aliphatic amide compound has preferably 19~60 carbon atoms, more preferably 19~50 carbon atoms in the molecular structure. Use of such aliphatic amide compound in combination provides a heat-sensitive recording material which is excellent in preservation stability of white portions and images, and particularly excellent in thermal response.

When the aliphatic amide compound has less than 18 carbon atoms in the molecular structure, the resulting heat-Sensitive recording material is inferior in preservation stability of white portions, particularly in heat resistance, and additionally its sensitivity for color development is insufficiently improved. On the other hand, the aliphatic amide compound having more than 60 carbon atoms in the molecular structure renders inferior preservation stability for the heat-sensitive recording material and is unfavorably difficult to obtain in some cases. The amount of the aliphatic amide compound is preferably 10–300% by weight, more preferably 20–200% by weight based on the salicylic acid derivative of the formula (1) or the metal salt of the derivative.

In the heat-sensitive recording material of the invention, a usually colorless or pale colored dyestuff precursor having electron donating ability and an electron accepting compound are generally used as principal components, these components are dispersed in a binder and coated on a substrate to form a heat-sensitive recording layer, and the layer is heated by a thermal head, hot pen or laser beam to develop recording images by an instantaneous reaction between the dyestuff precursor and the electron accepting compound. The process has been disclosed in Japanese Patent Publication SHO 43-4160 and 45-14039.

Fillers, sensitizers, antioxidants and antisticking agents are added to the heat-sensitive recording layer, when desired.

No particular restriction is imposed upon the dyestuff precursor for use in the heat-sensitive recording material of the invention as long as the dyestuff precursor is generally used for pressure-sensitive recording or heat-sensitive recording.

Practical electron donating compounds will be illustrated below.

(1) The triarylmethane compounds include, for example,
3,3-bis(4-dimethylaminophenyl)-6-dimethylaminophthalide [crystal violet lactone],
3,3-bis(4-dimethylaminophenyl)phthalide,
3-(4-dimethylaminophenyl)-3-(1,3-dimethylindol-3-yl)phthalide,
3-(4-dimethylaminophenyl)-3-(2-methylindol-3-yl)phthalide,
3,3-bis(9-ethylcarbazole-3-yl)-6-dimethylaminophthalide,
3-(4-dimethylaminophenyl)-3-(1-methylpyrrol-3-yl)6-dimethylaminophthalide, and
3,3-bis[2,2-bis(4-dimethylaminophenyl)ethenyl4,5,6,7-tetrachlorophthalide.

(2) Diarylmethane compounds include, for example,
4,4-bis-dimethylaminobenzhydrin benzyl ether,
N-halophenylleucoauramine, and
N-2,4,5-trichlorophenylleucoauramine.

(3) Rhodamine-lactam compounds include, for example,
rhodamine-B-anilinolactam, rhodammine-(4-nitroanilino)lactam, and
rhodamine-B-(4-chloroanilino)lactam.

(4) Fluoran compounds include, for example,
3,6-dimethoxyfluoran, 3-dimethylamino-7-methoxyfluoran,
3-diethylamino-6-methoxyfluoran, 3-diethylamino-7-methoxyfluoran,
3-diethylamino-7-chlorofluoran,
3-diethylamino-6-methyl-7-chlorofluoran,
3-diethylamino-6,7-dimethylfluoran,
3-N-cyclohexyl-N-n-butylamino-7-methylfluoran,
3-diethylamino-7-dibenzylaminofluoran,
3-diethylammino-7-octylaminofluoran,
3-diethylamino-7-di-n-hexylaminofluoran,
3-diethylamino-7-anilinofluoran,
3-diethylamino-7-(2-chloroanilino)fluoran,
3-diethylamino-7-(3-chloroanilino)fluoran,
3-diethylamino-7-(2,3-dichloroanilino)fluoran,
3-diethylamino-7-(3-trifluoromethylanilino)fluoran,
3-di-n-butylamino-7-(2-chloroanilino)fluoran,
3-diethylamino-6-chloro-7-anilinofluoran,
3-di-n-butylamino-6-chloro-7-anilinofluoran,
3-diethylamino-6-methoxy-7-anilinofluoran,
3-di-n-butylamino-6-ethoxy-7-anilinofluoran,
3-pyrrolidino-6-methyl-7-anilinofluoran,
3-morpholino-6-methyl-7-anilinofluoran,
3-dimethylamino-6-methyl-7-anilinofluoran,
3-diethylamino-6-methyl-7-anilinofluoran,
3-di-n-butylamino-6-methyl-7-anilinofluoran,
3-di-n-pentylamino-6-methyl-7-anilinofluoran,
3-di-n-octylamino-6-methyl-7-anilinofluoran,
3-N-ethyl-N-methylamino-6-methyl-7-anilinofluoran,
3-N-n-propyl-N-methylamino-6-methyl-7-anilinofluoran,
3-N-n-propyl-N-ethylamino-6-methyl-7-anilinofluoran,
3-N-isopropyl-N-methylamino-6-methyl-7-anilinofluoran,
3-N-n-butyl-N-methylamino-6-methyl-7-anilinofluoran,
3-N-n-butyl-N-ethylamino-6-methyl-7-anilinofluoran,
3-N-n-butyl-N-n-propylamino-6-methyl-7-anilinofluoran,
3-N-isobutyl-N-methylamino-6-methyl-7-anilinofluoran,
3-N-isobutyl-N-ethylamino-6-methyl-7-anilinofluoran,
3-N-isopentyl-N-ethylamino-6-methyl-7-anilinofluoran
3-N-n-hexyl-N-ethylamino-6-methyl-7-anilinofluoran,
3-N-n-octyl-N-ethylamino-6-methyl-7-anilinofluoran,
3-N-cyclohexyl-N-methylamino-6-methyl-7-anilinofluoran,
3-N-cyclohexyl-N-n-propylamino-6-methyl-7-anilinofluoran,
3-N-cyclohexyl-N-n-butylamino-6-methyl-7-anilinofluoran,
3-N-cyclohexyl-N-n-pentylamino-6-methyl-7-anilinofluoran,
3-N-cyclohexyl-N-n-hexylamino-6-methyl-7-anilinofluoran,
3-N-cyclohexyl-N-n-heptylamino-6-methyl-7-anilinofluoran,
3-N-cyclohexyl-N-n-octylamino-6-methyl-7-anilinofluoran,
3-N-cyclohexyl-N-n-decylamino-6-methyl-7-anilinofluoran,
3-N-2'-methoxyethyl-N-methylamino-6-methyl-7-anilinofluoran,
3-N-2'-methoxyethyl-N-ethylamino-6-methyl-7-anilinofluoran,
3-N-2'-methoxyethyl-N-isobutylamino-6-methyl-7-anilinofluoran,
3-N-2'-ethoxyethyl-N-methylamino-6-methyl-7-anilinofluoran,
3-N-2'-ethoxyethyl-N-ethylamino-6-methyl-7-anilinofluoran,
3-N-3'-methoxypropyl-N-methylamino-6-methyl-7-anilinofluoran,
3-N-3'-methoxypropyl-N-ethylamino-6-methyl-7-anilinofluoran,
3-N-3'-ethoxypropyl-N-methylamino-6-methyl-7-anilinofluoran,
3-N-3'-ethoxypropyl-N-ethylamino-6-methyl-7-anilinofluoran,
3-N-2'-tetrahydrofurfuryl-N-ethylamino-6-methyl-7-anilinofluoran,
3-N-(4'-methylphenyl)-N-ethylamino-6-methyl-7-anilinofluoran, 3-diethylamino-6-ethyl-7-anilinofluoran,
3-diethylamino-6-methyl-7-(3'-methylphenylamino)fluoran,
3-diethylamino-6-methyl-7-(2',6'-dimethylphenylamino)fluoran,
3-di-n-butylamino-6-methyl-7-(2',6'-dimethylphenylamino)fluoran,
3-di-n-butylamino-7-(2',6'-dimethylphenylamino)fluoran,
2,2-bis[4'-(3-N-cyclohexyl-N-methylamino-6-methylfluoran-7-ylaminophenyl]propane, and
3-[4'-(4-phenylaminophenyl)aminophenyl]amino-6-methyl-7-chlorofluoran.

(5) Indolylphthalide compounds include, for example,
3,3-bis(1-ethyl-2-methylindole-3-yl)phthalide,
3,3-bis(1-octyl-2-methylindole-3-yl)phthalide,
3-(2-ethoxy-4-diethylaminophenyl)-3-(1-ethyl-2-methylindole-3-yl)phthalide,
3-(2-ethoxy-4-dibutylaminophenyl)-3-(1-ethyl-2-methylindole-3-yl)phthalide, and
3-(2-ethoxy-4-diethylaminophenyl)-3-(1-octyl-2-methylindole-3-yl)phthalide.

(6) Pyridine compounds include, for example,
3-(2-ethoxy-4-diethylaminophenyl)-3-(1-octyl-2-methylindole-3-yl)-4 or 7-azaphthalide,
3-(2-ethoxy-4-diethylaminophenyl)-3-(1-ethyl-2-methylindole-3-yl)- 4 or 7-azaphthalide,
3-(2-hexyloxy-4-diethylaminophenyl)-3-(1-ethyl-2-methylindole-3-yl)-4 or 7-azaphthalide,
3-(2-ethoxy-4-diethylaminophenyl)-3-(1-ethyl-2-phenylindole-3-yl)-4 or 7-azaphthalide, and
3-(2-butoxy-4-diethylaminophenyl)-3-(1-ethyl-2-phenylindole-3-yl)-4 or 7-azaphthalide.

(7) Spiro compounds include, for example,
3-methyl-spiro-dinaphthopyran, 3-ethyl-spiro-dinaphthopyran,
3-phenyl-spiro-dinaphthopyran, 3-benzyl-spiro-dinaphthopyran,
3-methyl-naphtho-(3-methoxybenzo)spiropyran, and
3-propyl-spiro-dibenzopyran.

(8) Fluorene compounds include, for example,
3',6'-bis(diethylamino)-5-diethylaminospiro(isobenzofuran-1,9'-fluorene)-3-one, and
3',6'-bis(diethylamino)-7-diethylamino-2-methylspiro(1,3-benzoxazine-4,9'-fluorene).

These color forming, electron donating compounds can be used singly, or as a mixture in order to control color tone of developed image or to obtain multi-colored heat-sensitive recording materials.

The heat-sensitive recording material of the invention comprises as the electrons accepting compound one or more salicylic acid derivatives of the formula (1) and/or the metal salts of said derivatives. Other electron accepting compounds can be simultaneously used in the range giving no adverse effect on the desired properties of the heat-sensitive recording material of the invention.

No particular restriction is imposed on the electron accepting compound to be used in combination with the salicylic acid derivative of the invention as long as the compound is an acidic substance and is generally used for heat-sensitive recording materials. For example, phenol derivatives, aromatic carboxylic acid derivatives, N,N'-diarylthiourea derivatives, and zinc salt and other multivalent metal salts of organic compounds can be used.

Practical examples of particularly preferred phenol derivatives include phenol compounds such as p-phenyphenol,
p-hydroxyacetophenone, 4-hydroxy-4'-methyldiphenyl sulfone,
4-hydroxy-4'-isopropoxydiphenyl sulfone,
4-hydroxy-4'-benzenesulfonyloxydiphenyl sulfone,
1,1-bis(p-hydroxyphenyl)propane, 1,1-bis(p-hydroxyphenyl)pentane,
1,1-bis(p-hydroxyphenyl)hexane, 1,1-bis(p-hydroxyphenyl)cyclohexane,
2,2-bis(p-hydroxyphenyl)propane, 2,2-bis(p-hydroxyphenyl)hexane,
1,1-bis(p-hydroxyphenyl)-2-ethylhexane,
2,2-bis(3-chloro-4-hydroxyphenyl)propane,
1,1-bis(p-hydroxyphenyl)-1-phenylethane,
1,3-di-[2-(p-hydroxyphenyl)-2-propyl]benzene,
1,3-di-[2-(3,4-dihydroxydiphenyl)-2-propyl]benzene,
1,4-di-[2-(p-hydroxyphenyl)-2-propyl]benzene,
4,4'-dihydroxydiphenyl ether, 4,4'-dihydroxydiphenyl sulfone,
3,3'-dichloro-4,4'-dihydroxydiphenyl sulfone,
3,3'-diallyl-4,4'-dihydroxydiphenyl sulfone,
3,3'-dichloro-4,4'-dihydroxydiphenyl sulfide,
methyl-2,2-bis(4'-hydroxyphenyl)acetate,
n-butyl-4,4-(4'-hydroxyphenyl)acetate,
4,4'-thiobis(2-t-butyl-5-methylphenol), benzyl-p-hydroxybenzoate,
chlorobenzyl-p-hydroxybenzoate, dimethyl-4-hydroxyphthalate,
benzyl gallate, stearyl gallate, salicylic anilide, 5-chlorosalicylic anilide, salicylic acid, 3,5-di-tert-butylsalicylic acid,
3,5-di-α-methylbenzylsalicylic acid, 4-[2'-(4-methoxyphenyloxy)ethyloxy]salicylic acid,
and metal salts.

Exemplary binders which can be used for the heat-sensitive recording material of the invention include water soluble adhesives such as starches, hydroxyethylcellulose, methylcellulose, gelatin, casein, polyvinyl alcohol, modified polyvinyl alcohol, sodium polyacrylate, and alkali metal salt of acrylic amide/acrylic ester copolymer, acrylic amide/acrylic ester/methacrylic acid ternary copolymer, styrene/maleic anhydride copolymer and ethylene/maleic anhydride copolymer; and latexes such as polyvinyl acetate, polyurethane, polyacrylic ester, styrene/butadiene copolymer, acrylonitrile/butadiene copolymer, methyl acrylate/butadiene copolymer and ethylene/vinyl acetate copolymer.

Fillers which can be used include, for example, diatomaceous earth, talc, kaolin, calcined kaolin, calcium carbonate, magnesium carbonate, titanium oxide, zinc oxide, silicon oxide, aluminum hydroxide and urea-formaldehyde resin.

Metal salts of higher fatty acids such as zinc stearate and calcium stearate, and waxes such as paraffin, oxidized paraffin, polyethylene, oxidized polyethylene, stearic acid amide and castor wax can be added in order to prevent head abrasion and sticking. Dispersants such as sodium dioctylsulfosuccinate, benzophenone base and benzotriazol base ultraviolet absorbers, surface active agents and fluorescent dyes can also be added, if desired.

The substrate used for the invention is primarily paper. Non-woven fabrics, plastic films, synthetic paper, metal foil or composite sheets obtained by combination of these matters can also be arbitrarily used.

Further, application of an overcoat layer for protecting the heat-sensitive recording layer, application of single or more undercoat layers comprising fillers or resin between the heat-sensitive recording layer and the substrate, and a variety of other known techniques in the preparation of heat-sensitive recording materials can also be used in the invention.

The coating amount of the heat-sensitive recording layer depends upon the amounts of the dyestuff precursor and the electron accepting compound which are color developing components. The preferred amount of the dyestuff precursor is usually 0.1~1.0 g/m². The amount of the electron accepting compound is 5~700% by weight, preferably 20~500% by weight based on the dyestuff precursor.

Next, the present invention will be illustrated further in detail by way of examples. Part and percent in these examples are weight bases.

EXAMPLE 1

(A) Preparation of heat-sensitive coating liquid

In a ball mill, 35 parts of dyestuff precursor 3-dibutylamino-6-methyl-7-anilinofluoran was ground for 24 hours with 80 parts of a 2.5% aqueous polyvinyl alcohol solution to obtain a dyestuff dispersion. Separately, 40 parts of zinc 4-n-octyloxycarbonylaminosalicylate, 60 parts of stearoyl amide and 300 parts of a 2.5% aqueous polyvinyl alcohol solution were ground in a sand mill (Trade Mark: DYNOMILL, manufactured by WEB Co.) to obtain a dispersion of the electron accepting compound having a volume average particle size of 2 μm or less. The above two dispersions were mixed.

The following ingredients were added to the mixture with stirring and thoroughly mixed to obtain heat-sensitive coating liquid.

| | |
|---|---|
| 30% Dyestuff dispersion | 115 parts |
| 25% Electron accepting compound dispersion | 400 parts |
| 50% Aqueous calcium carbonate dispersion | 100 parts |
| 40% Aqueous zinc stearate dispersion | 25 parts |
| 10% Aqueous polyvinyl alcohol solution | 200 parts |
| Water | 280 parts |

(B) Preparation of paper to be used for heat-sensitive coating

A coating liquid having the formulation described below was applied on a base paper having a basis weight of 40 g/m² so as to obtain a solid coating weight of 9 g/m², and dried to obtain the paper to be used for heat-sensitive coating.

| | |
|---|---|
| Calcined Kaolin | 100 parts |
| 50% Aqueous styrene/butadiene latex | 24 parts |
| Water | 200 parts |

(C) Preparation of heat-sensitive recording material

The heat-sensitive coating liquid prepared in (A) was coated on the paper prepared in (B) so as to obtain a solid coating weight of 4 g/m², and dried to obtain a heat-sensitive recording material:

(D) Evaluation of the heat-sensitive recording material

The heat-sensitive recording material thus prepared was calendered so as to obtain 400–500 seconds in Beck smoothness of the heat-sensitive surface, and successively following evaluation tests were carried out. Results are summarized in Table 1.

(1) Color developing property (Heat response):

Evaluation was carried out with a color developing test.

[Color developing test]

A printing test was carried out using a facsimile tester TH-PMD (Trade Mark of Ohkura Electric Co.). A thermal head having a dot density of 8 dots/mm head resistance of 185Ω was used. Printing was carried out at a head voltage of 12 V and pulse duration of 0.7 and 1.0 millisecond. Developed color density was measured by a Macbeth Model RD-918 reflection densitometer.

When the developed color density is 0.90 and more under a pulse duration of 0.7 millisecond or 1.30 and more under a pulse duration of 1.0 millisecond in this test, the color developing property is determined good. Color density of less than these values indicates poor color developing property.

(2) Preservation property of white portions:

Evaluation was carried out with a heat resistance test and marker withstandability test.

[Heat resistance test of white portions]

To test heat resistance, each sample specimen of the heat-sensitive recording material was allowed to stand at 60° C. for 24 hours, thereafter whiteness of each sample specimen was measured by a Macbeth Model RD-918 reflection densitometer. The higher the value, the higher cooling—i.e. poorer heat resistance.

When the whiteness after the heat treatment is 0.20 or less, the heat resistance is determined good; when the value exceeds 0.20, the property determined poor reflecting degraded image quality that likely to occur on use depending on printing conditions or smudging of white background during storing.

[Marker withstandability of white background]

To test the marker withstandability, a mark was put, using a fluorescent maker, on the non-imaged portion of the specimen sheet, which in turn was allowed to stand for 72 hours under a room temperature. Thereafter, the unmarked portion was inspected visually and the results were reported as follows;

○ ... Substantially no smudging due to color development.

X ... Appreciably smudging due to color development.

(3) Preservation property of images:

Evaluation was carried out on three different scopes described as follows:

[Wrapping withstandability test]

A commercially available wrapping film was laid on each sample specimen that had been printed at 1.0 millisecond pulse duration and used in the aforesaid color development test. A weight rendering 2 g/cm² pressure is put on the wrapping film, and each of the thus wrapped and weight-loaded specimen sheet was allowed to stand for 24 hours at 40° C. Therafter, fading degree of the image was visually inspected, and the results were reported as follows;

○ ... Image preserved, i.e. substantially no fading.

X ... Image faded substantially, i.e. hardly legible.

[Marker withstandability test]

On each sample specimen that had been printed at 1.0 millisecond pulse duration and used in the color development test, a mark was put on the printed portion using a fluorescent marker. Each of the thus marked sample specimens was allowed to stand for 72 hours at room temperature. Thereafter, fading degree of the image was visually inspected, and the results were reported as follows;

○ ... Image preserved, i.e. substantially no fading.

X ... Image faded substantially, i.e. hardly legible.

[Wet heat resistance test]

Each sample specimen that had been printed at 1.0 millisecond pulse duration and used in the color development test was allowed to stand for 24 hors at 40° C. and under 90% RH (relative humidity).

The printed image does fade after having undergone this hot and moist environment. Image density of the color on each of the sample specimens, before and after this test, were measured by Mackbeth Model RD-918 reflection densitometer, and residual rate was calculated by the following equation;

$$\text{Residual rate (\%)} = \frac{\text{image density after the test}}{\text{image density before the test}} \times 100$$

Preservation stability is determined good when the residual rate is 70% or higher; preservation stability is determined excellent when the rate is 80% or higher.

EXAMPLE 2

A heat-sensitive recording material was prepared by carrying out the same procedures as described in Example 1 except that zinc 4-n-octyloxycarbonylaminosalicylate was replaced by zinc 4-n-decyloxycarbonylaminosalicylate.

The heat-sensitive recording material obtained was evaluated by the same procedures as Example 1.

EXAMPLE 3

A heat-sensitive recording material was prepared by carrying out the same procedures as described in Example 1 except that zinc 4-n-octyloxycarbonylaminosalicylate was replaced by zinc 4-phenyloxycarbonylaminosalicylate.

The heat-sensitive recording material obtained was evaluated by the same procedures as Example 1.

EXAMPLE 4

A heat-sensitive recording material was prepared by carrying out the same procedures as described in Example 1 except that stearic acid amide was replaced by behenic acid amide.

The heat-sensitive recording material obtained was evaluated by the same procedures as Example 1.

EXAMPLE 5

A heat-sensitive recording material was prepared by carrying out the same procedures as described in Example 1 except that stearic acid amide was replaced by N-hydroxymethylstearic acid amide.

The heat-sensitive recording material obtained was evaluated by the same procedures as Example 1.

EXAMPLE 6

A heat-sensitive recording material was prepared by carrying out the same procedures as described in Example 1 except that stearic acid amide was replaced by N-hydroxymethylbehenic acid amide.

The heat-sensitive recording material obtained was evaluated by the same procedures as Example 1.

EXAMPLE 7

A heat-sensitive recording material was prepared by carrying out the same procedures as described in Example 1 except that stearic acid amide was replaced by ethylenebisstearic acid amide.

The heat-sensitive recording material obtained was evaluated by the same procedures as Example 1.

EXAMPLE 8

A heat-sensitive recording material was prepared by carrying out the same procedures as described in Example 1 except that stearic acid amide was replaced by N-stearylstearic acid amide.

The heat-sensitive recording material obtained was evaluated by the same procedures as Example 1.

EXAMPLE 9

A heat-sensitive recording material was prepared by carrying out the same procedures as described in Example 1 except that stearic acid amide was replaced by N,N'-dioleylsebacic acid amide.

The heat-sensitive recording material obtained was evaluated by the same procedures as Example 1.

Comparative Example 1

A heat-sensitive recording material was prepared by carrying out the same procedures as described in Example 1 except that stearic acid amide was not used.

The heat-sensitive recording material obtained was evaluated by the same procedures as Example 1.

Comparative Example 2

A heat-sensitive recording material was prepared by carrying out the same procedures as described in Example 1 except that stearic acid amide was replaced by 2-benzyloxynaphthalene.

The heat-sensitive recording material obtained was evaluated by the same procedures as Example 1.

Comparative Example 3

A heat-sensitive recording material was prepared by carrying out the same procedures as described in Example 1 except that stearic acid amide was replaced by palmitic acid amide.

The heat-sensitive recording material obtained was evaluated by the same procedures as Example 1.

Comparative Example 4

A heat-sensitive recording material was prepared by carrying out the same procedures as described in Example 1 except that stearic acid amide was replaced by lauric acid amide.

The heat-sensitive recording material obtained was evaluated by the same procedures as Example 1.

Comparative Example 5

A heat-sensitive recording material was prepared by carrying out the same procedures as described in Example 1 except that zinc 4-n-octyloxycarbonylaminosalicylate was replaced by 2,2-bis(4-hydroxyphenyl)propane.

The heat-sensitive recording material obtained was evaluated by the same procedures as Example 1.

Comparative Example 6

A heat-sensitive recording material was prepared by carrying out the same procedures as described in Example 1 except that zinc 4-n-octyloxycarbonylaminosalicylate was replaced by zinc 3,5-bis(α-methylbenzyl)salicylate.

The heat-sensitive recording material obtained was evaluated by the same Procedures as Example 1.

TABLE 1

| Example or Comparative Example | Color density 0.7 m sec | Color density 1.0 m sec | Preservation stability White portion Heat resistance | Preservation stability White portion Marker withstand- ability | Preservation stability Image Wrapping withstand- ability | Preservation stability Image Marker withstand- ability | Wet heat resistance (%) |
|---|---|---|---|---|---|---|---|
| Example 1 | 0.97 | 1.35 | 0.15 | ○ | ○ | ○ | 71 |
| Example 2 | 1.05 | 1.36 | 0.16 | ○ | ○ | ○ | 70 |
| Example 3 | 0.90 | 1.32 | 0.13 | ○ | ○ | ○ | 73 |
| Example 4 | 0.98 | 1.35 | 0.13 | ○ | ○ | ○ | 86 |
| Example 5 | 0.95 | 1.33 | 0.17 | ○ | ○ | ○ | 85 |
| Example 6 | 0.98 | 1.35 | 0.17 | ○ | ○ | ○ | 88 |
| Example 7 | 0.94 | 1.33 | 0.16 | ○ | ○ | ○ | 83 |
| Example 8 | 0.93 | 1.35 | 0.18 | ○ | ○ | ○ | 80 |
| Example 9 | 0.90 | 1.35 | 0.18 | ○ | ○ | ○ | 82 |
| Com. Example 1 | 0.56 | 1.12 | 0.12 | ○ | ○ | ○ | 85 |
| Com. Example 2 | 0.79 | 1.25 | 0.13 | ○ | ○ | ○ | 80 |
| Com. Example 3 | 0.93 | 1.35 | 0.46 | ○ | ○ | ○ | 65 |
| Com. Example 4 | 0.90 | 1.32 | 0.68 | ○ | ○ | ○ | 67 |
| Com. Example 5 | 1.10 | 1.35 | 0.15 | Δ | x | x | 70 |
| Com. Example 6 | 1.06 | 1.32 | 0.65 | x | ○ | ○ | 72 |

What is claimed is:

1. A polyvalent metal salt of a salicylic acid derivative represented by the formula (1):

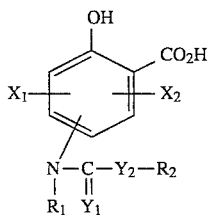

(1)

wherein $X_1$ and $X_2$ are a hydrogen atom, an alkyl group, an alkoxy group, an aralkyl group, an aryl group or a halogen atom, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group: with the proviso that when $X_1$, $X_2$ and $R_1$ each are a hydrogen atom, $Y_1$ and $Y_2$ both are an oxygen atom and $R_2$ is ethyl, the metal salt is not the calcium salt.

2. The metal salt of claim 1 wherein $X_1$ and $X_2$ are a hydrogen atom and $R_1$ is a hydrogen atom.

3. The metal salt of claim 1 wherein the metal salt is selected from the group consisting of a zinc, magnesium, calcium, barium, nickel, manganese, cobalt and aluminum salt.

4. The metal salt of claim 2 wherein the metal salt is selected from the group consisting of a zinc, magnesium, calcium, barium, nickel, manganese, cobalt and aluminum salt.

5. A process for preparing a salicylic acid derivative represented by the formula (1):

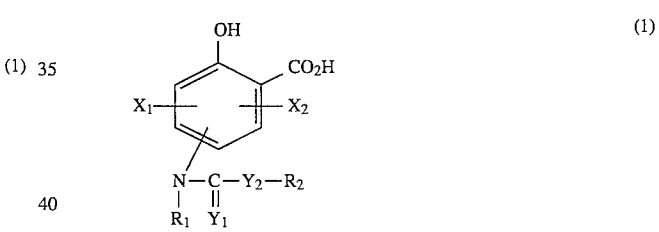

(1)

wherein $X_1$ and $X_2$ are a hydrogen atom, an alkyl group, an alkoxy group, an aralkyl group, an aryl group or a halogen atom, $Y_1$ and $Y_2$ are an oxygen atom or a sulfur atom, $R_1$ is a hydrogen atom, an alkyl group, an aralkyl group or an aryl group , and $R_2$ is an alkyl group, an alkenyl group, an aralkyl group or an aryl group, comprising reacting a compound represented by the formula (2):

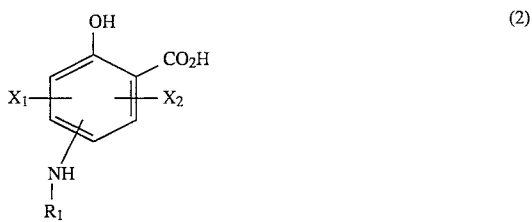

(2)

wherein X, $X_2$ and $R_1$ are the same as above, with a compound represented by the formula (3):

(3)

wherein $Y_1$, $Y_2$ and $R_2$ are the same as above and Z is a halogen atom, in the presence of an alcohol-based solvent.

6. A process for preparing a polyvalent metal salt of a salicylic acid derivative represented by the formula (1):

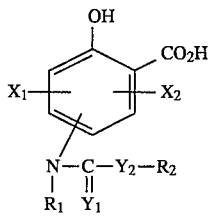 (1)

wherein $X_1$ and $X_2$ are a hydrogen atom, an alkyl group, an alkoxy group, an aralkyl group, an aryl group or a halogen atom, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, comprising reacting a compound represented by the formula (2):

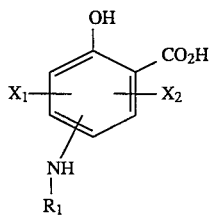 (2)

wherein $X_1$, $X_2$ and $R_1$ are the same as above, with a compound represented by the formula (3):

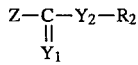 (3)

wherein $Y_1$, $Y_2$ and $R_2$ are the same as above and Z is a halogen atom, in the presence of an alcohol-based solvent, treating the resultant salicylic acid derivative represented by the formula (1) with an alkali metal salt, and carrying out a double decomposition reaction of the resulting alkali metal salt of the salicylic acid derivative in an aqueous solution with a water soluble compound of a metal having from 2 to 4 valence.

7. The metal salt of claim 1 wherein $X_1$, $X_2$ and $R_1$ each are a hydrogen atom, $Y_1$ and $Y_2$ each are an oxygen atom and the metal salt is the zinc salt.

8. The metal salt of claim 1 wherein $R_2$ is alkyl having from 3 to 24 carbon atoms, nonsubstituted or substituted alkenyl having from 2 to 24 carbon atoms, nonsubstituted or substituted aralkyl having from 7 to 24 carbon atoms, or nonsubstituted aryl having from 6 to 24 carbon atoms.

9. The metal salt of claim 1 wherein $R_2$ is n-octyl, n-decyl or phenyl.

10. The process of claim 5 wherein $R_2$ is alkyl having from 3 to 24 carbon atoms, nonsubstituted or substituted alkenyl having from 2 to 24 carbon atoms, nonsubstituted or substituted aralkyl having from 7 to 24 carbon atoms, or nonsubstituted aryl having from 6 to 24 carbon atoms.

11. The process of claim 5 wherein $X_1$, $X_2$ and $R_1$ each are a hydrogen atom, $Y_1$ and $Y_2$ each are an oxygen atom and the metal salt is the zinc salt.

12. The process of claim 5 wherein $R_2$ is n-octyl, n-decyl or phenyl.

13. The process of claim 6 wherein $R_2$ is alkyl having from 3 to 24 carbon atoms, nonsubstituted or substituted alkenyl having from 2 to 24 carbon atoms, nonsubstituted or substituted aralkyl having from 7 to 24 carbon atoms, or nonsubstituted aryl having from 6 to 24 carbon atoms.

14. The process of claim 6 wherein $X_1$, $X_2$ and $R_1$ each are a hydrogen atom, $Y_1$ and $Y_2$ each are an oxygen atom and the metal salt is the zinc salt.

15. The process of claim 6 wherein $R_2$ is n-octyl, n-decyl or phenyl.

* * * * *